(12) United States Patent
Vandroux et al.

(10) Patent No.: US 8,557,774 B2
(45) Date of Patent: Oct. 15, 2013

(54) RECOMBINANT PROTEINS HAVING HAEMOSTATIC ACTIVITY AND CAPABLE OF INDUCING PLATELET AGGREGATION

(75) Inventors: David Vandroux, Dijon (FR); Emmanuel De Maistre, Fontaine-les-Dijon (FR); Edouard Prost, Dijon (FR)

(73) Assignee: Centre Hospitalier Universitaire de, Dijon (FR)

( * ) Notice: Subject to any disclaimer, the term of this patent is extended or adjusted under 35 U.S.C. 154(b) by 0 days.

(21) Appl. No.: 13/120,838

(22) PCT Filed: Sep. 22, 2009

(86) PCT No.: PCT/EP2009/062271
§ 371 (c)(1),
(2), (4) Date: Mar. 24, 2011

(87) PCT Pub. No.: WO2010/034718
PCT Pub. Date: Apr. 1, 2010

(65) Prior Publication Data
US 2011/0207669 A1 Aug. 25, 2011

(30) Foreign Application Priority Data
Sep. 24, 2008 (FR) ...................................... 08 56423

(51) Int. Cl.
*A61K 38/00* (2006.01)

(52) U.S. Cl.
USPC ......... 514/13.8; 514/13.5; 514/21.2; 530/300

(58) Field of Classification Search
None
See application file for complete search history.

(56) References Cited

U.S. PATENT DOCUMENTS 8,080,515 B2 * 12/2011 Bouwstra et al. ................. 514/1
2004/0151731 A1 8/2004 Jicha

FOREIGN PATENT DOCUMENTS

WO 01/34647 5/2001

OTHER PUBLICATIONS

Kim J. K. et al; "A novel binding site in collagen type III for integrins alpha1beta1 and alpha2beta1." J. Biol. Chem. (2005) 280(37) p. 32512-32520.*
Farndale R. W. et al; "Cell-collagen interactions: the use of peptide toolkits to investigate collagen-receptor interactions." Biochem. Soc. Trans. ( Apr. 2008) 36 p. 241-250.*
Asselin J. et al; "Monomeric (glycine-proline-hydroxyproline)10 repeat sequence is a partial agonist of the platelet collagen receptoer glycoprotein VI." Biochem. J. (1999) 339, 413-418.*
Lisman, T. et al; "A single high affinity binding site for von Willebrand factor in collagen III, identified using synthetic triple helical peptides." Blood (2006) 108(12) 3753-3756.*
Pires, V. et al; "Type III collagen mimetic peptides designed with anti- or pro aggregant activities on human platelets." Eur. J. Med. Chem. (2007) 42 p. 694-701.*
Ruoslahti, E. "RGD and other recognition sequences for integrins." Annu. Rev. Cell. Dev. Biol. (1996) 13 p. 697-715.*
Sudo, T.; "Estimation of anti-platelet drugs on human platelet aggregtion with a novel whole blood aggregometer by a screen filtration pressure method." British Journal of Pharmacology, (2001) 133 p. 1396-1404.*
Toman et al.; "The Mouse Type-III Procollagen-Encoding Gene: Genomic Cloning and Complete DNA Sequence"; Gene; (1994) pp. 161-168; vol. 147.
Kim et al.; "A Novel Binding Site in Collagen Type III for Integrins alpha1beta1 and alpha2beta2"; The Journal of Biological Chemistry; Sep. 2005; pp. 32512-32520; vol. 280; No. 37.
Asselin et al.; "Monomeric (Glycine-Proline-Hydroxyproline)10 Repeat Sequence is a Partial Agonist of the Platelet Collagen Receptor Glycoprotein VI"; Biochem. J. (1999) 339; pp. 413-418.
Born; "Aggregation of Blood Platelets by Adenosine Diphosphate and Its Reversal"; 1962; Nature Publishing Group; pp. 927-929.
Boudko et al.; "Structure Formation in the C Terminus of Type III Collagen Guides Disulfide Cross-Linking"; J. Mol. Biol. (2004) 335, pp. 1289-1297.
Bulleid et al.; "Type-III Procollagen Assembly in Semi-Intact Cells: Chain Association, Nucleation and Triple-Helix Folding Do Not Require Formation of Inter-Chain Disulphide Bonds But Triple-Helix Nucleation Does Require Hydroxylation"; Biochem. J. (1996) 317, pp. 195-202.
Bulleid et al.; "The C-Propeptide Domain of Procollagen Can Be Replaced With a Transmembrane Domain Without Affecting Trimer Formation or Collagen Triple Helix Folding During Biosynthesis"; The EMBO Journal; 1997; pp. 6694-6701; vol. 16, No. 22.
Farndale et al.; "Cell-Collagen Interactions: The Use of Peptide Toolkits to Investigate Collagen-Receptor Interactions"; Biochem. Soc. Trans. (2008) pp. 241-250; 36.
Hulmes; "Building Collagen Molecules, Fibrils, and Suprafibrillar Structures"; Journal of Structural Biology; 137, 2-10 (2002).
Jarvis et al.; "Identification of a Major GPVI-Binding Locus in Human Type III Collagen"; 2008 111: 4986-4996; Prepublished Online Feb. 27, 2008.
Verkleij et al.; Simple Collagen-Like Peptides Support Platelet Adhesion Under Static But Not Under Flow Conditions: Interaction Via Alpha 2beta 1 and Von Willebrand Factor With Specific Sequences in Native Collagen Is a Requirement to Resist Shear Forces; 1998; 91; pp. 3808-3816.
Lisman et al.; "A Single High-Affinity Binding Site for Von Willebrand Factor in Collagen III, Identified Using Synthetic Triple-Helical Peptides"; 2006 108: 3753-3756; Preprinted Online Aug. 15, 2006.
McAlinden et al.; "Alpha-Helical Coiled-Coil Oligomerization Domains Are Almost Ubiquitous in the Collagen Superfamily"; The Journal of Biological Chemisty; Issue of Oct. 24, 2003; pp. 42200-42207; vol. 278, No. 43.
Monnet et al.; "A New Platelet Receptor Specific to Type III Collagen"; The Journal of Biological Chemistry; Issue Apr. 14, 2000; pp. 10912-10917, vol. 275, No. 15.

(Continued)

*Primary Examiner* — Cecilia J Tsang
*Assistant Examiner* — Fred Reynolds
(74) *Attorney, Agent, or Firm* — Miles & Stockbridge, PC

(57) ABSTRACT

Disclosed herein are recombinant proteins capable of inducing platelet aggregation and uses thereof.

6 Claims, 6 Drawing Sheets

(56) References Cited

OTHER PUBLICATIONS

Morton et al.; "Integrin alpha2beta1-Independent Activation of Platelets by Simple Collagen-Like Peptides: Collagen Tertiary (Triple-Helical) and Quaternary (Polymeric) Structures Are Sufficient Alone for alpha2beta1-Independent Platelet Reactivity"; Biochem. J. (1995) pp. 337-344; 306.

Olsen et al.; "Recombinant Collagen and Gelatin for Drug Delivery"; Advanced Drug Delivery Reviews 55 (2003) pp. 1547-1567.

Pires et al.; "Type III Collagen Mimetic Peptides Designed With Anti- or Pro-Aggregant Activities on Human Platelets"; European Journal of Medicinal Chemistry 42 (2007) pp. 694-701.

Raynal et al.; "Use of Synthetic Peptides to Locate Novel Integrin alpha2beta1-Binding Motifs in Human Collagen III"; The Journal of Biological Chemistry; vol. 281; No. 7; pp. 3821-3831, Feb. 17, 2006.

Ruggiero et al.; "Making Recombinant Extracellular Matrix Proteins"; Methods 45 (2008) pp. 75-85.

Smethurst et al.; "Structural Basis for the Platelet-Collagen Interaction"; The Journal of Biological Chemistry; vol. 282, No. 2, pp. 1296-1304; Jan. 12, 2007.

International Search Report Based on PCT/EP2009/062271 Mailed Feb. 9, 2010.

* cited by examiner

SEQUENCE LISTING

```
<160> NUMBER OF SEQ ID NOS: 8

<210> SEQ ID NO 1
<211> LENGTH: 152
<212> TYPE: PRT
<213> ORGANISM: Artificial Sequence
<220> FEATURE:
<223> OTHER INFORMATION: Coll-III-like recombinant protein

<400> SEQUENCE: 1

Met Met Ser Phe Val Gln Lys Gly Ser Trp Leu Leu Leu Ala Leu Leu
1               5                   10                  15

His Pro Thr Ile Ile Leu Ala Gln Gly Arg Pro Gly Ala Pro Gly Glu
            20                  25                  30

Arg Gly Leu Pro Gly Pro Pro Gly Pro Arg Gly Ala Ala Gly Glu Pro
        35                  40                  45

Gly Arg Asp Gly Val Pro Gly Gly Pro Gly Met Arg Gly Met Pro Gly
    50                  55                  60

Ser Pro Gly Gly Pro Gly Ser Asp Gly Lys Pro Gly Pro Pro Gly Ser
65                  70                  75                  80

Gln Gly Glu Ser Gly Arg Pro Gly Pro Gly Glu Asn Gly Lys Pro
                85                  90                  95

Gly Glu Pro Gly Pro Lys Gly Asp Ala Gly Pro Pro Gly Pro Pro Gly
            100                 105                 110

Pro Pro Gly Pro Pro Gly Pro Pro Gly Pro Pro Gly Pro Pro Gly Pro
        115                 120                 125

Pro Gly Pro Pro Gly Pro Pro Gly Pro Arg Gly Asp Lys Gly Pro Pro
    130                 135                 140

Gly Ala Pro Gly Pro Cys Pro Gly
145                 150

<210> SEQ ID NO 2
<211> LENGTH: 459
<212> TYPE: DNA
<213> ORGANISM: Artificial Sequence
<220> FEATURE:
<223> OTHER INFORMATION: Sequence coding for recombinant Coll-III-like
      protein

<400> SEQUENCE: 2
atgatgagct tcgtgcagaa ggggagctgg ctgcttctcg ctctgcttca tcctactatt      60
atcctggcac aggggcgccc cggagctcct ggagagagag gattgcctgg acctccaggg     120
```

-continued

```
cccagaggag ctgctggaga acctggcaga gatggcgtcc ctggaggacc aggaatgagg      180
ggcatgcccg gaagcccagg aggaccagga agcgatggga agccagggcc tcccggaagc      240
cagggagaaa gcggcagacc aggacctcct ggagagaacg gaaagcctgg agaaccaggc      300
ccaaagggag atgccggacc acctggccca ccaggccctc ccggaccacc tggacctcca      360
ggccctcctg gccctcctgg acctcctgga ccacctggac ctccaggccc aagaggcgac      420
aagggacctc ctggagcccc tggaccttgc cctggctaa                             459
```

<210> SEQ ID NO 3
<211> LENGTH: 21
<212> TYPE: DNA
<213> ORGANISM: Artificial Sequence
<220> FEATURE:
<223> OTHER INFORMATION: Sense primer (S)

<400> SEQUENCE: 3

```
agctggcgcg ccgccaccat g                                                21
```

<210> SEQ ID NO 4
<211> LENGTH: 27
<212> TYPE: DNA
<213> ORGANISM: Artificial Sequence
<220> FEATURE:
<223> OTHER INFORMATION: Antisense primer (AS)

<400> SEQUENCE: 4

```
gcttccggga ggccctggct tcccatc                                          27
```

<210> SEQ ID NO 5
<211> LENGTH: 69
<212> TYPE: DNA
<213> ORGANISM: Artificial Sequence
<220> FEATURE:
<223> OTHER INFORMATION: tagNVH001-sense primer

<400> SEQUENCE: 5

```
gctgccatgg gcagcagcca tcatcatcat catcacggtc gcccgggagc tcctggagag      60
agaggattg                                                              69
```

<210> SEQ ID NO 6
<211> LENGTH: 38
<212> TYPE: DNA
<213> ORGANISM: Artificial Sequence
<220> FEATURE:
<223> OTHER INFORMATION: tagNVH001-antisense primer

<400> SEQUENCE: 6

```
gcacggatcc tattagccag ggcaaggtcc aggggctc                              38
```

<210> SEQ ID NO 7
<211> LENGTH: 6
<212> TYPE: PRT
<213> ORGANISM: Artificial Sequence
<220> FEATURE:
<223> OTHER INFORMATION: Peptide motif

<400> SEQUENCE: 7

Gly Ala Pro Gly Glu Arg
1               5

<210> SEQ ID NO 8
<211> LENGTH: 8
<212> TYPE: PRT

```
-continued

<213> ORGANISM: Artificial Sequence
<220> FEATURE:
<223> OTHER INFORMATION: Peptide motif

<400> SEQUENCE: 8

Lys Pro Gly Glu Pro Gly Pro Lys
1               5
```

RECOMBINANT PROTEINS HAVING HAEMOSTATIC ACTIVITY AND CAPABLE OF INDUCING PLATELET AGGREGATION

CROSS REFERENCE TO RELATED APPLICATIONS

This application is a §371 National Stage Application of PCT/EP2009/062271 filed Sep. 22, 2009, which claims priority to French Application No. 085 64 23 filed Sep. 24, 2008.

BACKGROUND OF THE INVENTION

1. Field of the Invention

The present invention relates to recombinant proteins composed of the assembly of the peptide sequences described for interacting with platelet collagen receptors. These proteins have a pro-aggregating activity, independent of the formation of a triple helix. They can be produced in bacteria and in mammalian cells.

2. Description of Related Art

Collagens are the principal structural components of the extracellular matrix of all multicellular organisms. They are a family of proteins composed of 28 different types that play a role during development and in tissue homeostasis. They are capable of being assembled into various supramolecular structures in the form of fibrils, microfibrils or networks.

Collagens have the common characteristic of containing one or more domains that have a triple helix structure formed of three polypeptide chains, or α chains, coiled together. As all three are amino acids, this characteristic is enabled by the presence of a glycine in the helicoidal motifs which consist of repeated G-X-Y sequences where X is often a proline and Y a hydroxyproline. This hydroxyproline is essential to the stabilisation of the triple helix and is characteristic of collagens. The proline residues are hydroxylated primarily by prolyl-4-hydroxylase (P-4-H) into 4-hydroxyproline. There is a second hydroxylase, prolyl-3-hydroxylase, which enables the hydroxylation of proline when it is in position X, whereas in position Y a proline hydroxylated by P-4-H is already found. In a collagen molecule, the alpha chains can be identical or different.

Collagen molecules are formed of helicoidal domains (or collagenous domains) flanked by non-helicoidal domains, called N- and C-propeptides. Recognition of the three α chains that form a molecule and the start of their assembly are under the control of the C-terminal end (C-propeptide). This process is carried out at the endoplasmic reticulum. Subsequently, the N- and C-propeptides are excised during collagen maturation, leaving short non-helicoidal sequences, telopeptides.

Collagens play an important role at the vessel walls by maintaining their integrity and their elasticity. This wall is formed of type-I collagen and type-III collagen, which are fibrillar, and of type-IV collagen, in network form. It should be noted that type-III collagen is also strongly expressed at atheromatous plaques. Furthermore, collagens are capable of modulating the functions of certain cells by direct interaction with specific cellular receptors. Thus, collagens, mainly types I and III, are powerful activators of platelet function.

Type-III collagen is a homotrimer composed of three α1 chains arranged in a triple helix. Two G-P-P triplets (potentially hydroxylated), present at the C-terminal end of the α1 chains, are then sufficient and necessary to the nucleation and the folding of the triple helix (Bulleid et al., *EMBO J.* 1997 Nov. 17; 16(22): 6694-701). On the other hand, these two triplets are not sufficient to enable the initial combining of the three chains. It is interesting to note that Bulleid et al. (1997) observed greater efficiency of triple helix formation when three triplets are maintained, and this efficiency is even greater than for the wild molecule. Several proteins are involved in the assembly process of monomeric chains: HSP47 (heat shock protein) and PDI (protein disulfide isomerase). C-propeptide, located at the C-terminal end of monomeric chains, appears involved in the alignment of α chains and the formation of the disulfide bridges necessary to the stabilisation of the protein (Bulleid et al., *EMBO J.* 1997 Nov. 17; 16(22): 6694-701). This C-propeptide is thus necessary only to ensure the combining of the monomeric chains. Various points should be remembered in relation to it:

- It consists of a discontinuous sequence of 15 amino acids which determines the specific standard assembly of α1 chains (Hulmes D J, *J Struct Biol.* 2002 January-February; 137(1-2): 2-10).
- A coiled-coil domain located at the beginning of the C-propeptide is involved in the trimerisation of collagen III (Bulleid et al., *EMBO J.* 1997 Nov. 17; 16(22): 6694-701). This domain consists of four heptapeptides (McAlinden et al., *J Biol Chem.* 2003 Oct. 24; 278 (43): 42200-7).
- It contains eight cysteine residues which enable the formation of intra- and intercatenary disulfide bridges.

The presence of disulfide bridges between chains at the C-telopeptide or C-propeptide is not necessary for the combining of the chains and the formation of the triple helix (Bulleid et al., *Biochem J.* 1996 Jul. 1; 317(Pt 1): 195-202). It should be noted that the experiments are undertaken with the N-propeptide. The notions of trimer and of alpha triple helix seem paradoxically independent. In the absence of N-propeptide, it seems judicious to leave either cysteine 2 of the C-propeptide, or the two cysteines of the C-telopeptide. This latter motif, called the knot sequence (GPCCG), enables the formation of disulfide bridges only by virtue of a preliminary phenomenon of assembly and folding of the α1 chains (Boudko and Engel, *J Mol Biol.* 2004 Jan. 30; 335(5): 1289-97).

Whether of traumatic origin or the consequence of atherosclerosis, damage to the arterial wall is accompanied by the destruction of the vascular endothelium and the exposure of thrombogenic components such as collagen. This is followed by adhesion of platelets at the damaged site, in contact with surfaces rich in collagen or collagen fragments, their activation and the formation of a thrombus. The adhesion and stabilisation of the platelets in contact with this collagen are enabled by multiple interactions, of high affinities, between receptors present at the surface of the platelets and the collagen. This adhesion can occur indirectly following the binding of the A1 domain of the von Willebrand factor (vWF) with the platelet complex formed of the glycoproteins (Gp) GpIb-V-IX, itself bound to collagen by its A3 domain, or by direct interaction between a platelet receptor and collagen. Several receptors can bind collagen molecules at highly specific peptide sequences, namely integrin α2β1, which plays an important role in the stabilisation of the platelet in contact with collagen, and GpVI, considered as the most important receptor for platelet activation. Another receptor, TIIICBP (type-III collagen-binding protein), has been described as capable of binding collagen directly.

Blood vessel flow rate is a major determinant that defines the type of platelet collagen receptors recruited. At an elevated flow rate, the platelets interact with collagen via vWF via the GpIb receptor and then they are activated by binding via GpVI; integrin α2β1 only intervenes as a stabiliser of the platelet-collagen bond. At a low flow rate, the platelets bind to collagen via integrin α2β1, followed by binding to GpVI, thus leading to their activation, which is the step that prepares platelet aggregation. Similarly, other platelet collagen receptors are involved such as TIIICBP. In all cases, GpVI plays a major role in platelet activation.

Platelet adhesion is a process that is now dissociated from platelet activation. Indeed, many peptides, corresponding to short peptide motifs of collagen, are capable of inducing the adhesion of platelets without leading to their activation. Nevertheless, some of these peptides have the capacity to induce platelet activation and exhibit a so-called pro-aggregating activity. Their triple helix structure seems to be an essential prerequisite for this activity. It should be noted that when some of these peptides remain in monomeric form, they exhibit an anti-aggregating activity by a mechanism which remains to be identified but which could be the occupation of sites that become unavailable for native collagen.

Most of the work aimed at identifying the peptide sequences involved in the adhesion of platelets with type-III collagen use the fragment α1(III) CB4 corresponding to the digestion fragment by CNBr exhibiting the highest aggregating activity.

Various peptide motifs have been described in the past few years as being capable of binding and activating platelets. They have been tested in the form of peptides of two possible natures:
  similar to collagen, formed by the repetition of conserved GPO motifs repeated n times, not present in the native sequence of type-III collagen;
  or corresponding to peptides formed of peptide motifs present in the α1(III) CB4 sequence, principally obtained by chemical synthesis (Farndale et al., *Biochem Soc Trans*. 2008 April; 36(Pt 2): 241-50).

Integrin α2β1 is a receptor for collagens, laminin and other ligands in various cell types including endothelial cells and platelets. α2β1 binds collagen via its domain I at the peptide motifs present in the sequence of fibrillar collagens. Various motifs have been described with the highest affinity for GFOGER present at the α1 chain of type-I collagen. For type-III collagen, and contrary to type-I collagen, it seems that several GXYGER motifs are necessary for optimal binding, with GLOGER, GMOGER, GROGER and GAOGER as principal motifs (Kim et al., *J Biol Chem*. 2005 Sep. 16; 280(37): 32512-20). Other motifs such as GLOGEN and GLKGEN have been described but exhibit low affinity for α2β1 (Raynal et al., *J Biol Chem*. 2006 Feb. 17; 281(7): 3821-31). It should be noted that all of the peptides synthesised from these motifs exhibit an adhesion activity when they are organised in the form of a triple helix.

Glycoprotein VI (GPVI) is a 60-65 kDa type-I transmembrane glycoprotein belonging to the immunoglobulin (Ig) superfamily. It is constitutively expressed on the surface of platelets in the form of a non-covalent complex with the γ chain common to Ig receptors (FcRγ). The peptides described as interacting with this receptor are peptides similar to collagen formed from the repetition of 4 to 10 GPO triplets (Morton et al., *Biochem J*. 1995 Mar. 1; 306(Pt 2): 337-44 and Smethurst et al., *J Biol Chem*. 2007 Jan. 12; 282(2): 1296-304). Although comprising 10% GPO motifs, the maximum number of repetitions of this triplet does not exceed three in the native sequence of type-III collagen. It should be further noted here that the formation of the triple helix or of a polymeric form, obtained chemically following a modification of the cysteine or lysine residues, is essential to confer on these peptides a pro-aggregating activity. Moreover, the presence of a hydroxyproline in position 3 is essential to this activity. Conversely, when they are in monomeric form, these peptides exhibit an anti-aggregating activity (Asselin et al., *Biochem J*. 1999 Apr. 15; 339 (Pt 2): 413-8). Recently, Jarvis et al. identified the peptide motif in the type-III collagen sequence that exhibits the highest adhesion activity. It is composed of residues GAOGLRGGAGPOGPEGGKGAAGPOGPO located at amino acids 523 to 549 of α1(III) CB4 (Jarvis et al., *Blood*. 2008 May 15; 111(10): 4986-96). This peptide motif is composed of three GPO, which are not consecutive and which seems to be the minimal number necessary for proper interaction with GpVI.

Indirect interaction between the platelet receptor GpIb and collagen is dependant on vWF, which is a plasma multimeric protein secreted by endothelial cells and platelets in response to vascular damage or following an increase in parietal pressure. It plays a major role in the recruitment of platelets at damaged sites of vascular territories subjected to elevated flow rates. This factor is composed of three domains named A1, A2 and A3. It binds collagen via its A3 domain and binds the GpIb receptor by its A1 domain. Type-III collagen seems to have a single site, of high affinity for the A3 domain of vWF, which is also present in type-II collagen. This peptide motif is located between amino acids 403 and 413 and is composed of GPRGQOVMGFO with certain amino acids critical for binding vWF (Lisman T et al., *Blood*. 2006 Dec. 1; 108(12): 3753-6). Verkleij et al. identified as a potential binding site amino acids 541 to 558 composed of GAAGPOG-POGSAGTOGLQ (Verkleij et al., *Blood*. 1998 May 15; 91(10): 3808-16). This peptide motif is located between the vWF motif described by Lisman et al. and the GMOGER integrin α1β2 binding motif.

The Fauvel-Lafève team described the existence of an octapeptide, KOGEOGPK, located between amino acids 655 and 662 of the fragment α1(III) CB4. The platelet receptor recognised by this octapeptide has been identified and named TIIICBP (type-III collagen binding protein) (Monnet E et al., *J Biol Chem*. 2000 Apr. 14; 275(15): 10912-7). This octapeptide is capable of inhibiting the interaction of platelets with type-III collagen, but not with type-I collagen, under both static and flow conditions. More recently, Pires et al. showed that this octapeptide has an inhibiting activity on aggregation only when it is in homotrimer form. On the contrary, its structure in triple helix form by adding at these ends cysteines and GPP gives it a pro-aggregating activity (Pires et al., *Eur J Med Chem*. 2007 May; 42(5): 694-701).

The biological and ultrastructural properties of collagens, and notably their capacity of binding to membrane receptors, open a broad field of applications because of their multiple roles in tissues. However, these applications only have meaning if it is possible to have homogeneous preparations of these collagens in large quantities and in a reproducible way.

Two methods of production were used to this end. The work and developments conducted in these two areas are generally highly targeted for a given application. Thus, chemical synthesis can produce short peptides that represent only a tiny part of the protein, in general peptide motifs of interest. Its principal application relates to haemostasis and more precisely to modulation of the bond between collagen and platelets.

However, these peptides have in general only one of the activities sought and this can depend on the three-dimensional conformation of the peptide and notably of the formation of a triple helix. Thus, there is a significant need for the development of functionalised recombinant collagen proteins that can be produced by biological systems offering high productivity. A major obstacle is the difficulties of production and purification of these collagen-derived proteins because of their tendency to aggregate and to adhere.

To date, short peptide sequences (fewer than 50 amino acids) have all been produced by chemical synthesis and not via cellular production systems (Farndale et al., *Biochem Soc Trans.* 2008 April; 36(Pt 2): 241-50). Moreover, these motifs have been synthesised in an isolated way. Conversely, the synthesis of recombinant type-III collagen, exhibiting platelet binding activity, has been carried out via cellular production systems and it is the totality of the sequence, for example proα1(III), which has been used. The objective sought is the synthesis of a whole procollagen capable of being organised into a triple helix (WO 9 307 889). These recombinant collagens have in principle multiple applications, namely those of the complete collagen sequence.

It is thus a question of synthesising smaller proteins of simpler structure that are thus less demanding in terms of production but that preserve the biological activities of interest of the native protein.

SUMMARY OF THE INVENTION

The invention thus relates to recombinant proteins possessing the motifs necessary to obtain a pro-aggregating activity, synthesised in the form of a monomer incapable of being structured into the form of a triple helix. The impossibility of forming this triple helix is the consequence of the absence of: I) α chain recognition motifs between them, II) non-helicoidal collagen N- and C-terminal domains as well as III) two GPO triplets necessary to the priming of the triple helix. Surprisingly, pro-aggregating activity is obtained in the absence of the formation of a triple helix.

The Applicant has shown in a surprising way that it is possible to bring together three types of peptide sequences within a single monomeric protein having pro-aggregating activity.

The recombinant proteins of the present invention thus bring together:
  peptide motifs with at least one repetition of four GPO triplets,
  peptide sequences described as having binding activity to the various platelet receptors present in the native collagen sequence,
  binding sequences between these motifs formed of the repetition of GXY triplets.

The production of these proteins by bacteria and mammalian cells makes it possible to have in large quantities these new-generation recombinant collagens, fruits of the combination of peptide sequences similar to collagen and sequences present in the native form of collagen. These types of proteins do not require favouring cells that do not produce collagens constitutively as host cells for this production. Indeed, their sequence does not allow recognition of the alpha chains of various native collagens. On the contrary, it is necessary to favour collagen-producing cells that express key enzymes of collagen maturation such as prolyl-4-hydroxylase (P4H) and HSP47. Current recombinant collagen production systems to the contrary use cells that do not naturally produce collagen (Olsen et al., *Adv Drug Deliv Rev.* 2003 Nov. 28; 55(12): 1547-67 and Ruggiero and Koch, *Methods.* 2008 May; 45(1): 75-85). This involves cotransfecting the gene coding for enzymes such as P4H.

The recombinant proteins according to the invention have many advantages, including:
  bringing together motifs of interest within small proteins that are easier to produce using cellular production systems,
  pro-aggregating activity in the absence of a triple helix structure,
  the absence in their sequence of collagenase recognition sites but the presence of HSP47 recognition sites, enabling their production by collagen-producing cells,
  their biological activity shown by reference tests (platelet aggregation tests) which are used for monitoring current antiplatelet treatments and for exploring platelet functions.

The biological properties of the recombinant proteins according to the invention make it possible to envisage many applications.

The first application relates to the use of these proteins as a diagnostic tool in the exploration of thrombotic disease: platelet aggregation tests, in vitro thrombosis models and evaluation of the effectiveness of current antiplatelet treatments (aspirin, clopidogrel) and future treatments. The proteins produced are derived from human proteins and have in their sequence binding sites for certain platelet receptors described for their role in platelet adhesion and activation. Current tests use collagens of animal origin whose sequences do not have perfect homology with those of humans. Furthermore, variation of the number and location of platelet receptor interaction sites between the various proteins makes it possible to propose more relevant target validation tests. There are peptide fragments that make it possible to work more specifically on each platelet receptor but their method of production is different from that of the invention, with chemical synthesis versus natural production by cells (importance of post-translational modifications).

The present invention can play a part in the composition of haemostatic bandages (thus strengthening on-site recruitment of platelets in the case of vascular lesion), or of haemostatic adhesives to prevent the risk of bleeding (surgical context). Products are currently on the market, but with a collagen of animal origin.

Another application is the use of these proteins to activate cicatrisation. Cicatrisation of certain wounds requires the on-site migration, adhesion and differentiation of certain cell populations, including platelets. These processes are dependant on the surface integrins of these cells. Certain peptide motifs present in the structure of the inventive proteins are thus capable of interacting with these integrins by promoting cicatrisation.

In a very close field, these recombinant proteins could be proposed in the composition of certain dermatological creams.

Another application of proteins that inhibit platelet function is the treatment of atherothrombosis. Platelet receptors are therapeutic targets with a future for fighting complications of atherothrombotic disease. To date, there is no molecule capable of blocking the initial phase of platelet adhesion in the subendothelium. The various protein structures of the inventive proteins enable their interaction with these receptors leading to platelet anti-adhesion effects (site masking) and/or platelet pro-adhesion effects. The various effects can be obtained with the same protein by modulating its physicochemical properties.

This invention thus provides a biological reagent with numerous applications that can play a part in the composition of kits: to evaluate platelet functions, to activate cell differentiation for the diagnosis of haematological dysfunctions, to detect by imaging areas of fibrosis. This invention can also enter in the composition of haemostatic bandages for the on-site recruitment of platelets (in the case of vascular lesion), haemostatic adhesives to prevent the risk of bleeding, or dermatological creams.

DESCRIPTION OF SEQUENCES

SEQ ID No. 1: Coll-III-like recombinant protein
SEQ ID No. 2: Polynucleotide coding for Coll-III-like recombinant protein
SEQ ID Nos. 3-6: Primers

DESCRIPTION OF THE INVENTION

The invention relates to isolated polypeptides that have the sequence of the polypeptide of SEQ ID No. 1 or the polypeptide of position 25 to position 152 of SEQ ID No. 1.

The invention also relates to isolated polypeptides with at least 70% identity over their entire length with the polypeptide of SEQ ID No. 1 or with the polypeptide of position 25 to position 152 of SEQ ID No. 1, and capable of inducing an aggregation of human blood platelets greater than 30% in a platelet aggregometer at 37° C. with stirring of 1000 rpm.

In a preferred embodiment, these polypeptides comprise the following peptide motifs:
  $GX_1X_2GER$ wherein $X_1$ and $X_2$ represent independently an amino acid selected from A, R, N, D, Q, E, G, H, I, K, M, F, P, S, T, W, Y, V and O;
  $(GPX_3)n$ with n between 4 and 10 and $X_3$ representing P or O;
  $GPRGQX_4GVMGFX_5$ where $X_4$ and $X_5$ represent independently P or O.
P is proline and O is hydroxyproline.

In another preferred embodiment, these polypeptides comprise the following peptide motifs:
  GAPGER,
  KPGEPGPK,
  (GPP)n with n between 4 and 10,
  RGD.

The invention also relates to an isolated polynucleotide characterised in that it codes for a polypeptide according to the invention.

In a preferred embodiment, the polynucleotide has the sequence of the polynucleotide of SEQ ID No. 2.

The invention also relates to an antibody binding specifically to the polypeptide of SEQ ID No. 1.

The invention also relates to expression cassettes comprising in the direction of transcription:
  a functional promoter in a host organism,
  a polynucleotide according to the invention,
  a functional termination sequence in the same host organism.

The invention also relates to a vector comprising a polynucleotide according to the invention and/or an expression cassette according to the invention.

The invention also relates to a host organism transformed with a polynucleotide according to the invention, an expression cassette according to the invention and/or a vector according to the invention.

The invention also relates to compositions for use as a drug comprising a polypeptide according to the invention, a polynucleotide according to the invention, an expression cassette according to the invention, a vector according to the invention and/or a host organism according to the invention.

In a preferred embodiment, the invention relates to compositions for the treatment of thrombotic diseases.

In another preferred embodiment, the invention relates to compositions for the treatment of disorders of haemostasis.

The invention also relates to the use of these compositions as a cicatrisation agent.

Lastly, the invention relates to cosmetic compositions comprising a polypeptide such as described above.

The invention relates to isolated polypeptides having the sequence of the polypeptide of SEQ ID No. 1 or the polypeptide of position 25 to position 152 of SEQ ID No. 1.

The peptide of position 1 to position 24 of SEQ ID No. 1 corresponds to the signal peptide that enables secretion of the recombinant protein by a host cell. This signal peptide can be absent or be replaced by another signal peptide according to techniques well known to the person skilled in the art. The person skilled in the art will be able to choose the homologous or heterologous signal peptide suitable for the expression and secretion of the polypeptides of the present invention in various prokaryotic or eukaryotic expression systems. Preferably, the polypeptides of the present invention are produced in eukaryotic cells or organisms and in particular in mammalian cells. In a particular embodiment of the invention, the polynucleotides of the present invention comprise a signal peptide enabling their secretion in the extracellular medium. In another embodiment, the invention relates to the mature polypeptide obtained after cleavage of the signal peptide.

The polypeptides of the present invention have a biological activity and notably a pro-aggregating activity on human blood platelets detected using a platelet aggregometer (Regulest, Florange, France), according to the reference technique (Born, 1962). Platelet-rich plasma (PRP) is brought into contact with an agonist (10 μl in 290 μl PRP) and the clearing of the medium (related to the formation of aggregates which fall to the bottom of the tube) is monitored in real time (aggregation curve). In the absence of platelet aggregation, the signal remains flat (persistent turbid medium). It is possible to verify the absence or presence of aggregates by examination of the tube at the end of measurement. Evaluation of the platelet aggregation test response is carried out at 37° C., with continuous stirring (1000 rpm). The apparatus is calibrated as follows: 0% aggregation with platelet-rich plasma (preparation obtained by slow centrifugation and concentration adjusted to $300 \times 10^9/L$) and 100% aggregation with platelet-poor plasma (preparation obtained by rapid centrifugation). The quality of the platelet preparations was validated by verifying the response to reference agonists (5 μM ADP and 1 μg/ml collagen), used for the development of antiplatelet therapeutics. A protein is considered pro-aggregating when it is capable of inducing aggregation greater than 30%, and in an irreversible way.

The receptor recognition peptide motifs expressed on the surface of many cell types confer on the polypeptide activity of the following types:
  cell adhesion,
  cell recruitment.

The pro-aggregating effect of the polypeptide, independent of its triple helix structure, is the consequence of the activation of one or more receptors present on the platelet surface ($\alpha1\beta2$, TIIICBP and GPVI).

The invention also relates to fragments of the polypeptide of SEQ ID No. 1 that preserve at least one of the activities of the polypeptide of SEQ ID No. 1. The term "fragment" of a polypeptide indicates a polypeptide comprising a part but not the totality of the polypeptide from which it is derived. The invention thus relates to a polypeptide comprising a fragment of at least 100, 110, 120, 130, 140 or 150 amino acids of the polypeptide of SEQ ID No. 1.

These fragments of the polypeptide of SEQ ID No. 1 preserve at least one of the activities of the polypeptide of SEQ ID No. 1, in particular pro-aggregating activity on human blood platelets. The invention thus relates to the biologically active fragments of the polypeptide of SEQ ID No. 1. The term "biologically active fragment" indicates a fragment of a polypeptide that preserves the function of the polypeptide from which it is derived. The biologically active fragments of the polypeptide of SEQ ID No. 1 thus preserve at least one of the functions of this polypeptide and preferably preserve all the biological activities of the polypeptide of SEQ ID NO. 1. The methods for preparing fragments of a polypeptide as well as the techniques for measuring the biological activities of the polypeptides of the present invention are well known to the person skilled in the art.

The invention also relates to polypeptides that have at least one of the activities of the polypeptide of SEQ ID No. 1 and with amino acids at least 70% identical to the polypeptide of SEQ ID No. 1. Preferably, these polypeptides have the same properties and notably the same biological activities as the polypeptide of SEQ ID No. 1. The invention relates to polypeptides with amino acids at least 70%, 80%, 90%, 95%, 98% and preferentially at least 99% identical to the polypeptide of SEQ ID No. 1. "Identical amino acids" means amino acids that are invariant or unchanged between two sequences. These polypeptides can have a deletion, an addition or a substitution of at least one amino acid compared to the polypeptide of SEQ ID No. 1.

The invention also relates to polypeptides with at least 70%, 80%, 90%, 95%, 98% and preferentially at least 99% homology with the polypeptide of SEQ ID No. 1. "Homology" means the measurement of the resemblance between protein sequences. These polypeptides can have a deletion, an addition or a substitution of at least one amino acid compared to the polypeptide of SEQ ID No. 1. The degree of homology between two sequences, quantified by a score, is based on the percentage of identities and/or preserving substitutions of the sequences.

The polypeptides of the present invention with a certain degree of homology or identity with the polypeptide of SEQ ID No. 1 comprise at least 100 or 150 amino acids.

Methods for measuring and identifying the degree of identity and the degree of homology between polypeptides are known to the person skilled in the art. The AlignX alignment tool (Clustal W algorithm) of the Vector NTi 9.1.0 software package (Invitrogen INFORMAX, http://www.invitrogen.com), for example, can be used, preferably using the default settings.

The polypeptides according to the invention are isolated or purified from their natural environment. The polypeptides can be prepared by means of various methods. These methods are notably production of recombinant polypeptides by suitable host cells and their subsequent purification, production by chemical synthesis or, finally, a combination of these various approaches. These various production methods are well known to the person skilled in the art. Preferably, the polypeptides of the present invention are produced by recombinant prokaryotic or eukaryotic cells. The polypeptides of the present invention can thus be produced in bacteria or in mammalian cells.

The invention also relates to fusion proteins, proteins or chimeric proteins comprising the polypeptides according to the invention. The term "polypeptide" indicates proteins as well as modified polypeptides.

In one embodiment of the invention, the polypeptides according to the invention are glycosylated. The polypeptide of SEQ ID No. 1 has notably O-glycosylation sites on the lysine amino acids present in positions 102 and 141 (in position 3 of a GXY triplet). In a preferred embodiment, the asparagine residue in position 93 of the polypeptide of SEQ ID No. 1 is glycosylated.

The invention also relates to polynucleotides coding for the polypeptides defined above. According to the present invention, "polynucleotide" means a single-strand nucleotide chain or its DNA or RNA complement, or a double-strand nucleotide chain which can be of complementary or genomic DNA. Preferably, the polynucleotides of the invention are DNA, in particular double-strand DNA. The term "polynucleotide" also means modified polynucleotides. The polynucleotides of the present invention are isolated or purified from their natural environment. Preferably, the polynucleotides of the present invention can be prepared by the classic molecular biology techniques as described by Sambrook et al. (*Molecular Cloning: A Laboratory Manual,* 1989) or by chemical synthesis.

In a first embodiment, the invention relates to the polynucleotide of SEQ ID No. 2. In a second embodiment, the invention relates to the polynucleotide of SEQ ID No. 2 whose sequence lies between position 73 and position 459 of SEQ ID No. 1. These polynucleotides code for the polypeptides defined above.

The invention also relates to polynucleotides with at least 70%, 75%, 80%, 85%, 90%, 95%, 98% and preferably at least 99% identity with the polynucleotide of SEQ ID No. 2 or with the polynucleotide whose sequence lies between position 73 and position 459 of SEQ ID No. 2. These polynucleotides code preferably for a polypeptide that preserves the biological activities of the polypeptide of SEQ ID No. 1.

"Identical nucleotides" means nucleotides that are invariant or unchanged between two sequences. These polynucleotides can have a deletion, an addition or a substitution of at least one nucleotide compared to the reference polynucleotide.

The invention also relates to polynucleotides with at least 70%, 75%, 80%, 85%, 90%, 95%, 98% and preferably at least 99% homology with the polynucleotide of SEQ ID NO. 2 or with the polynucleotide whose sequence lies between position 73 and position 459 of SEQ ID No. 2. These polynucleotides code preferably for a polypeptide that preserves the biological activities of the polypeptide of SEQ ID No. 1.

"Homology" means the measurement of the resemblance between nucleic sequences. These polynucleotides can have a deletion, an addition or a substitution of at least one nucleotide compared to the reference polynucleotide. The degree of homology between two sequences, quantified by a score, is based on the percentage of identities and/or preserving substitutions of the sequences.

Methods for measuring and identifying the degree of identity and the degree of homology between nucleic acid sequences are well known to the person skilled in the art. The AlignX alignment tool (Clustal W algorithm) of the Vector NTi 9.1.0 software package (Invitrogen INFORMAX, http://www.invitrogen.com), for example, can be used, preferably using the default settings.

The invention also relates to polynucleotides capable of hybridising selectively with the polynucleotide of SEQ ID NO. 2 or with the polynucleotide whose sequence lies between position 73 and position 459 of SEQ ID No. 2. Preferably, selective hybridisation is carried out under conditions of medium stringency and preferentially under conditions of high stringency. These polynucleotides code preferably for polypeptides having the biological activities of the polypeptide of SEQ ID No. 1. "Sequence capable of hybridising selectively" means, according to the invention, the sequences that hybridise with the reference sequence at a level significantly greater than the background noise. The signal level generated by the interaction between the sequence capable of hybridising selectively and the reference sequences is generally 10 times more intense, preferably 100 times more intense than that of the interaction of the other DNA sequences generating the background noise. The stringent hybridisation conditions that enable selective hybridisation are well known to the person skilled in the art. In general, the hybridisation and washing temperature is at least 5° C. lower than the Tm of the reference sequence at a given pH and for a given ionic strength. Typically, the hybridisation temperature is at least 30° C. for a polynucleotide of 15 to 50 nucleotides and at least 60° C. for a polynucleotide of more than 50 nucleotides. For example, hybridisation is carried out in the following buffer: 6×SSC, 50 mM Tris-HCl (pH 7.5), 1 mM EDTA, 0.02% PVP, 0.02% Ficoll, 0.02% BSA, 500 µg/ml denatured salmon sperm DNA. Washings, for example, are carried out successively with low stringency in 2×SSC, 0.1% SDS buffer, with medium stringency in 0.5×SSC, 0.1% SDS buffer and with high stringency in 0.1×SSC, 0.1% SDS buffer. Hybridisation can of course be carried out according to other common methods well known to those persons skilled in the art (see in particular Sambrook et al., *Molecular Cloning: At Laboratory Manual,* 1989). Preferably, the polynucleotides that hybridise selectively to a reference polynucleotide preserve the function of the reference sequence.

The invention generally relates to polynucleotides coding for the polypeptides according to the invention. Due to degeneration of the genetic code, different polynucleotides can code for the same polypeptide.

The invention also relates to an antibody binding specifically to the polypeptide of SEQ ID No. 1.

"Binding specifically" means that these antibodies bind only to the polypeptide of SEQ ID No. 1. In particular, the antibodies do not bind to other antigens and notably not to other collagenous proteins.

The antibodies according to the present invention are preferably specific monoclonal antibodies, notably of murine origin, chimeric or humanised which could be obtained according to standard methods well known to the person skilled in the art.

In general, the techniques for preparing monoclonal antibodies or their functional fragments, notably of murine origin, can be selected from those described in particular in the handbook Antibodies (Harlow and Lane, Antibodies: A Laboratory Manual, Cold Spring Harbor Laboratory, Cold Spring Harbor N.Y., p. 726, 1988) or the hybridoma-based preparation technique well known to the person skilled in the art. "Antibody" also means chimeric or humanised antibodies.

The invention also relates to expression cassettes comprising in the direction of transcription:
 a functional promoter in a host organism,
 a polynucleotide according to the invention,
 a functional termination sequence in the same host organism.

According to one embodiment of the invention, a polynucleotide coding for a polypeptide according to the invention is inserted in an expression cassette by using cloning techniques well known to the person skilled in the art. This expression cassette comprises the elements necessary to the transcription and translation of sequences coding for the polypeptides according to the invention.

Advantageously, this expression cassette comprises at the same time elements that cause a host cell to produce a polypeptide and elements necessary to the regulation of this expression.

Any type of promoter sequence can be used in the expression cassettes according to the invention. The choice of promoter will depend notably on the host organism chosen for the expression of the gene of interest. Certain promoters enable constitutive expression whereas other promoters are on the contrary inducible. Among the functional promoters in bacteria, that of the bacteriophage T7 RNA polymerase can be cited in particular. Among the functional promoters in yeasts, the GAL1 gene promoter or the GAL4 and ADH promoters of *S. cerevisiae* can be cited. Among the functional promoters in higher eukaryotic cells and notably in mammalian cells, CMV (cytomegalovirus), SV40, RSV (Rous sarcoma virus), human or chicken beta-actin, beta-globin, PGK (phosphoglycerate kinase), EF1alpha, thymidine kinase, and MMTV (mouse mammary tumour virus) can be cited. All these promoters are described in the literature and are well known to the person skilled in the art.

Expression cassettes, according to the present invention, can further include any other sequence necessary to the expression of polypeptides or polynucleotides such as, for example, regulation elements or signal sequences enabling the secretion of polypeptides produced by the host organism. Any regulation sequence that increases the level of expression of the coding sequence inserted in the expression cassette can be notably used. According to the invention, other regulation sequences, which are located between the promoter and the coding sequence, such as transcription activators ("enhancers"), can notably be used in combination with the promoter regulation sequence.

A wide variety of termination sequences can be used in the expression cassettes according to the invention; these sequences enable the termination of transcription and mRNA polyadenylation. Any functional termination sequence in the selected host organism can be used.

The present invention also relates to a polynucleotide comprising an expression cassette according to the invention, advantageously the expression cassettes according to the present invention are inserted in a vector.

The present invention thus also relates to replication or expression vectors for the transformation of a host organism comprising at least one polynucleotide or expression cassette according to the present invention. This vector can notably correspond to a plasmid, a cosmid, a bacteriophage or a virus in which is inserted a polynucleotide or an expression cassette according to the invention. The techniques for constructing these vectors and for inserting in these vectors a polynucleotide of the invention are well known to the person skilled in the art. Generally, any vector capable of being maintained, capable of self replicating or capable of propagating in a host cell in order to induce notably the expression of a polynucleotide or a polypeptide can be used. The person skilled in the art will choose suitable vectors according to the host organism to be transformed, and according to the transformation technique used.

The vectors of the present invention are notably used to transform a host organism with a view to the replication of the vector and/or the expression of a polypeptide according to the invention in the host organism.

The invention also relates to a method for preparing a polypeptide according to the invention comprising the following steps:
 a host organism is transformed with an expression vector comprising an expression cassette according to the invention and/or with a polynucleotide according to the invention,
 the polypeptides produced by the host organism are isolated.

The present invention also relates to a method for transforming a host organism by integrating in the aforementioned host organism at least one polynucleotide or expression cassette or vector according to the invention. The polynucleotide can be integrated in the genome of the host organism or replicated in a stable manner in the host organism. Methods for transforming host organisms are well known to the person skilled in the art and are widely described in the literature.

The present invention also relates to a host organism transformed with a polynucleotide, expression cassette or vector according to the invention. "Host organism" means in particular according to the invention any unicellular or multicellular, lower or higher organism, in particular selected from bacteria, yeasts and cells of higher eukaryotes, in particular mammalian cells such as CHO (Chinese hamster ovary cells), BHK (baby hamster kidney), HEK-293 (human embryonic kidney cell line), NSO (mouse myeloma cell line), Per.C6 (Crucell), and YB2/0 (ATCC no. CRL 1662). "Host organism" means a nonhuman organism.

The invention also relates to compositions for use as a drug comprising a polypeptide according to the invention, a polynucleotide according to the invention, an expression cassette according to the invention, a vector according to the invention and/or a host organism according to the invention. The invention thus also relates to pharmaceutical compositions comprising a polypeptide according to the invention, a polynucleotide according to the invention, an expression cassette according to the invention, a vector according to the invention and/or a host organism according to the invention.

In a preferred embodiment, the invention relates to compositions for the prevention and/or the treatment of thromboses.

In another embodiment, the invention relates to compositions for the prevention or the treatment of disorders of haemostasis.

The invention also relates to said compositions for use as a cicatrisation agent.

In another embodiment, the inventive compositions can also be used as:
- diagnostic reagents for detecting:
  - certain platelet dysfunctions
  - haematological diseases
- active components of haemostatic bandages and adhesives in the composition of dermatological and cosmetic creams.

The invention also relates to therapeutic methods for treating thromboses comprising the administration to an individual of an effective quantity of a polypeptide according to the invention, a polynucleotide according to the invention, an expression cassette according to the invention, a vector according to the invention and/or a host organism according to the invention.

The invention relates lastly to the use of the polypeptides, polynucleotides and transformed host organisms of the present invention for the manufacture of drugs.

The invention relates to pharmaceutical compositions comprising a polypeptide, polynucleotide or transformed host organism such as defined in the present invention and a suitable pharmaceutical excipient.

Said compositions can be formulated for administration to mammals, including humans. The dosing regimen varies according to the treatment and the disease in question. Said compositions are prepared in such a way as to be capable of being administered by the digestive or parenteral route.

In the pharmaceutical compositions of the present invention for oral, sublingual, subcutaneous, intramuscular, intravenous, transdermal, local or rectal administration, the active ingredient can be administered in unit forms of administration, in mixture with classic pharmaceutical carriers, to animals or humans. Suitable unit forms of administration comprise forms by oral route such as tablets, gelatin capsules, powders, granules and oral solutions or suspensions; sublingual and buccal forms of administration; subcutaneous, intramuscular, intravenous, intranasal or intraocular forms of administration; and rectal forms of administration.

When a solid composition in tablet form is prepared, the principal active ingredient is mixed with a pharmaceutical excipient such as gelatin, starch, lactose, magnesium stearate, talc, gum arabic or analogues. Tablets can be coated with saccharose or other suitable materials or can be treated in such a way that they have extended or delayed activity and that they continuously release a predetermined quantity of active ingredient.

A preparation in gelatin capsules is obtained by mixing the active ingredient with a diluent and by pouring the mixture obtained into soft or hard gelatin capsules.

A preparation in syrup or elixir form can contain the active ingredient together with a sweetener, an antiseptic, as well as a flavouring agent and a suitable colorant.

Water-dispersible powders or granules can contain the active ingredient in mixture with dispersion or wetting agents, or suspension agents, as well as with flavour correctors or sweeteners.

The invention also relates to cosmetic compositions comprising a polypeptide as described above.

These compositions can moreover comprise active ingredients classically used in dermatology such as emollients, hydrating active ingredients, cutaneous barrier restructuring agents, anti-irritants, and soothing agents. The cosmetic compositions according to the invention can be formulated in the form of various preparations suitable for topical application. According to a preferred embodiment, the various preparations are suitable for topical application and include creams, emulsions, milks, pomades, lotions, oils, aqueous or hydroalcohol or glycol solutions, powders, sprays, jellies, gels, hydrogels or any other product for external application. These cosmetic compositions can also contain antioxidants, preservatives, etc. The invention further relates to a method of cosmetic treatment, hygienic care, or embellishment and/or a method to perfume mucosa and/or skin that is normal, dry, oily, mixed, dehydrated, aged, sensitive, irritated, uncomfortable, intolerant, with an imbalance related to intrinsic, extrinsic or hormonal ageing or related to exogenic attack (pollutants, UV, stress, etc.), with allergic tendency, or with pigmentation disorders, characterised in that it consists in applying a composition according to the invention.

BRIEF DESCRIPTION OF THE DRAWINGS

FIG. 2 represents platelet aggregation induced by the conditioned medium (CM) of adherent CHO-S cells, transfected in a transitory fashion, in the presence or absence of epinephrine.

FIG. 3 represents expression of messenger RNA coding for the protein in a stable cell clone.

FIG. 4 shows detection by Western blotting of the presence of protein-6X-histidine in the various bacterial fractions obtained after purification.

FIG. 5 shows platelet aggregation induced by the protein produced in bacteria.

FIG. 6 shows validation by Western blotting of the specificity of the rabbit serum obtained after 89 days of immunisation.

EXAMPLES

A. Transitory Production by Mammalian Cells

1. Vector Construction

Plasmid 1 (NVH001-A)

Plasmid NVH001-A contains the following elements:
- an intron from plasmid pCIneo (Promega: pCIneo Mammalian Expression Vector)
- the inventive protein NVH001 from vector pUC57-NVH001 (ordered from GeneCust) and possessing type-III collagen signal peptide (NP_000081)
- a polyA tail from hGH mRNA (NM_000515)
- a CMV promoter from pCDF1-MCS1-EF1-copGFP (System Biosciences: pCDF cDNA Cloning and Expression Lentivectors).

Plasmid 2 (NVH001-B1), 3 (NVH001-B2), 4 (NVH001-C1) and 5 (NVH001-C2)

Plasmids NVH001-B1 and NVH001-C1 contain the following elements:
- an SV40 origin from derived plasmid pSV2-Neo (ori SV40:1-989 in vector ATCC 37149)
- a promoter/enhancer that can be one of those described in Molecular Cloning: A Laboratory Manual: 3rd edition, Sambrook and Russell, 2001, Cold Spring Harbor Laboratory Press
- a hygromycin cassette from pMono-hygro-mcs (Invitrogen)
- the inventive protein NVH001 from vector pUC57-NVH001 (ordered from GeneCust) and possessing type-III collagen signal peptide (NP_000081)
- a C-propeptide from plasmid pUC57-proC (ordered from GeneCust)
- a polyA tail from hGH mRNA (NM_000515).

Plasmids NVH001-B2 and NVH001-C2 contain the same elements as plasmids NVH001-B1 and C1 except C-propeptide.

All the final plasmids are sequenced to verify that no mutation was introduced in the DNA of the protein of interest and in the elements provided.

2. Transfection of Mammalian Cells

Plasmid 1 (NVH001-A)

1. Vector NVH001-A is transfected, in a transitory fashion, in CHO-S cells made adherent and cultivated in RPMI medium containing 5% foetal calf serum using the Lipofectamine 2000 kit from Invitrogen.

2. The culture supernatants are collected at days 3 and 4, the proteins produced are purified and then their platelet binding activity is tested using an aggregometer.

Plasmids 2 (NVH001-B1), 3 (NVH001-B2), 4 (NVH001-C1) and 5 (NVH001-C2)

1. Vectors NVH001-B1, NVH001-B2, NVH001-C1 and NVH001-C2 are transfected in a transitory fashion in CHO-S cells made adherent and cultivated in RPMI medium containing 5% foetal calf serum using the Lipofectamine 2000 kit from Invitrogen.

The RNA of the transfected cells are extracted at days 1, 2, 3, 4 and 5 by the adding of 800 µl of TRIZOL (Invitrogen). The corresponding cDNA are obtained by reverse transcription from 1 µg total RNA. Amplification by PCR was carried out on the cDNA. Amplicons are then detected after migration on a 2% agarose gel for 30 minutes at 125 V. A positive control (transfected plasmid) and a negative control were also carried out. The molecular weight marker (at left) is used to verify amplicon size.

Figure 1:
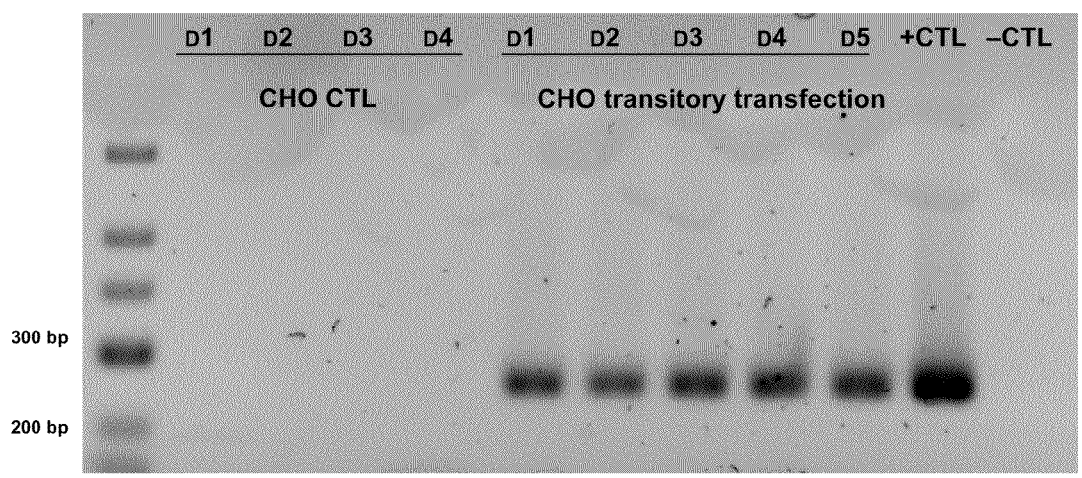
FIG. 1: Expression of messenger RNA coding for the protein in adherent CHO-S cells transfected in a transitory fashion.

Expression in the cells transfected with mRNA coding for the inventive protein is observed as of day 1. This expression increases slightly over time and is maintained after 5 days. The progress of mRNA expression is represented in FIG. 1.

2. The culture supernatants are collected at days 3 and 4, the proteins produced are purified and then their platelet binding activity is tested using an aggregometer.

3. Biological Activity of the Inventive Protein: Platelet Aggregation

The platelet binding activity of the inventive protein is evaluated by aggregometry. Blood samples in citrate tubes, collected from healthy volunteer donors after signed consent, are centrifuged at 150 g for 15 minutes in order to obtain platelet-rich plasma (PRP). Concentration is adjusted to 300 giga/L. Aggregation tests are carried out using a Reguest® platelet aggregometer, with stirring (1000 rpm) at 37° C. This technique is based on photometric reading according to the Born method which consists in measuring the evolution of the light transmission of a turbid medium, PRP, in response to a platelet function activator. If platelet aggregates are formed, the medium clears up and an increase in light transmission is observed. A molecule is considered to have a pro-aggregating effect when an increase of more than 30% is observed in this transmission associated with a break in the slope corresponding to this clearing.

Figure 2:
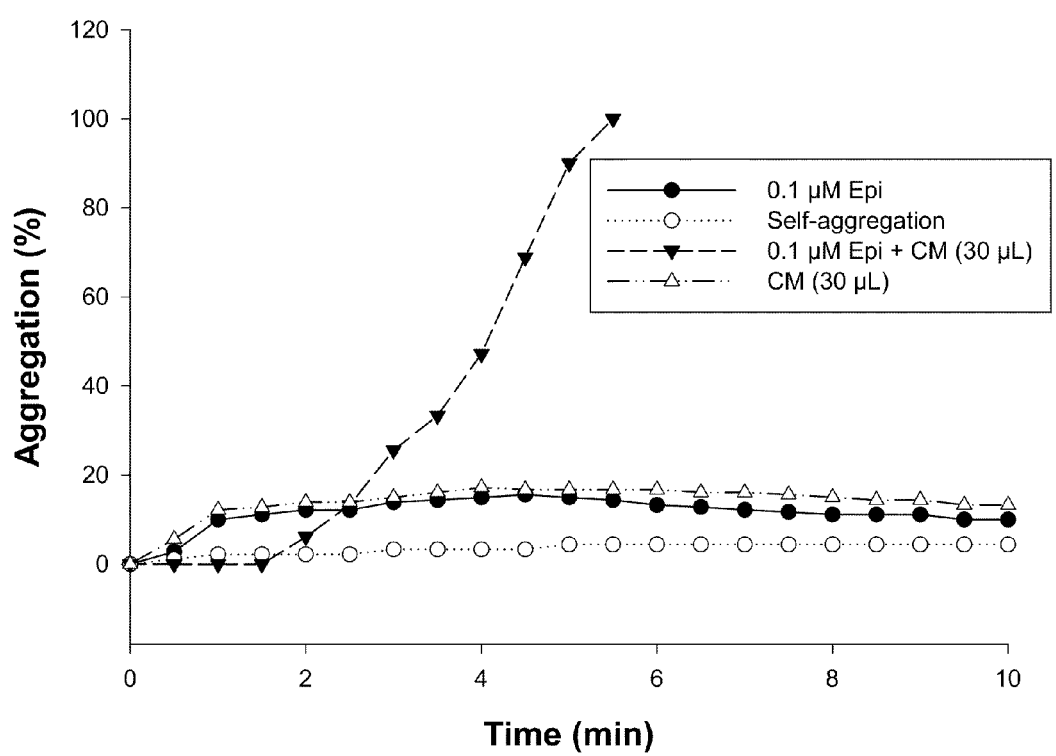
FIG. 2.

FIG. 2 represents platelet aggregation induced by the conditioned medium of adherent CHO-S cells, transfected in a transitory fashion, in the presence or absence of epinephrine.

The reaction mixture is composed of 290 µl PRP to which is added 30 µl conditioned medium in the presence or absence of 0.1 µM epinephrine. Platelet response is measured for 10 minutes. Self-aggregation (-○-) defines the baseline. Adding 0.1 µM epinephrine induces a slight shift of the baseline, stable for 10 minutes (-●-). Adding 30 µl conditioned medium induced a limited response (18%) after 2 minutes (-∇-). This shift is stable during the 10 minutes of observation. Adding epinephrine for 2 minutes, followed by adding 30 µl conditioned medium induced total platelet aggregation in 5 minutes (-▼-). This aggregation is not reversible, suggesting that the aggregates formed are stable.

Adding 30 µl of conditioned medium of non-transfected adherent CHO-S cells does not induce aggregation (result not presented).

B. Stable Production by Mammalian Cells

1. Vector Construction

Plasmid 1 (NVH001-A)

1. The intron-NVH001-hGHpA unit is removed from the vector constructed for transitory expression and is cloned in a production vector containing a hygromycin cassette from pMono-hygro-mcs (Invitrogen).

2. The final vector is sequenced to verify that no mutation was introduced in the DNA of the protein of interest and in the elements provided.

3. The linearised vector is transfected in a stable fashion in CHO cells made adherent using the Lipofectamine 2000 kit from Invitrogen. The transfected cells are selected by progressive levels of hygromycin B.

Figure 3:
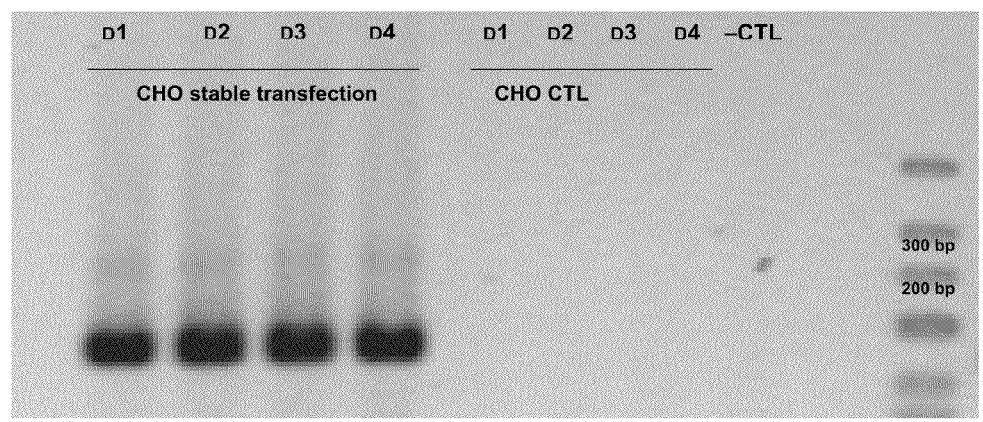
FIG. 3.

FIG. 3 represents expression of messenger RNA coding for the protein in a stable cell clone.

Cell RNA are extracted at days 1, 2, 3 and 4 by the adding of 800 µl TRIZOL (Invitrogen). The corresponding cDNA are obtained by reverse transcription from 1 µg total RNA. PCR amplification was carried out on cDNA using 5'-AGCTG-GCGCGCCGCCACCATG-3' (S) and 5'-GCTTCCGGGAG-GCCCTGGCTTCCCATC-3' (AS) primers. Amplicons are then detected after migration on a 2% agarose gel for 30 minutes at 125 V. A positive control, corresponding to plasmid DNA, is used. The molecular weight marker (at right) is used to verify amplicon size. Stable expression is observed in the cell clone.

C. Production in Bacteria

1. Construction

The DNA of the molecule of interest (NVH001) is amplified by PCR on the vector pUC57-NVH001 using the tag-NVH001'-sense primer: GCTGCCATGGGCAGCAGCCAT-CATCATCATCATCACGGTCGCCCGGGAGCTCCTGG AGAGA GAGGATTG and the tagNVH001'-antisense primer: GCACGGATCCTATTAGCCAGGGCAAG-GTCCAGGGGCTC which makes it possible to add a 6X-histidine tag on the N-terminal side of protein NVH001. The PCR products are cloned in vector pET3d (pET3d-NVH001) enabling production of the molecule in bacteria (New England Biolab).

The presence and the correct sequence of the DNA are verified by sequencing.

2. Production

1. The vector pET3d-NVH001 is transfected in BL21 bacteria enabling the mass production of protein.

2. The bacteria are inoculated in 1 l nutritive medium and are incubated at 37° C. until $OD_{600nm}$ is obtained in which the bacteria are in exponential phase.

3. Protein production is induced by IPTG for 5 hours at 30° C.

4. The bacteria are pelleted, lysed and the inventive protein is purified in the soluble (supernatant) and insoluble (inclusion body) fraction of the bacteria on Macherey-Nagel anti-6X-histidine tag columns.

Figure 4:
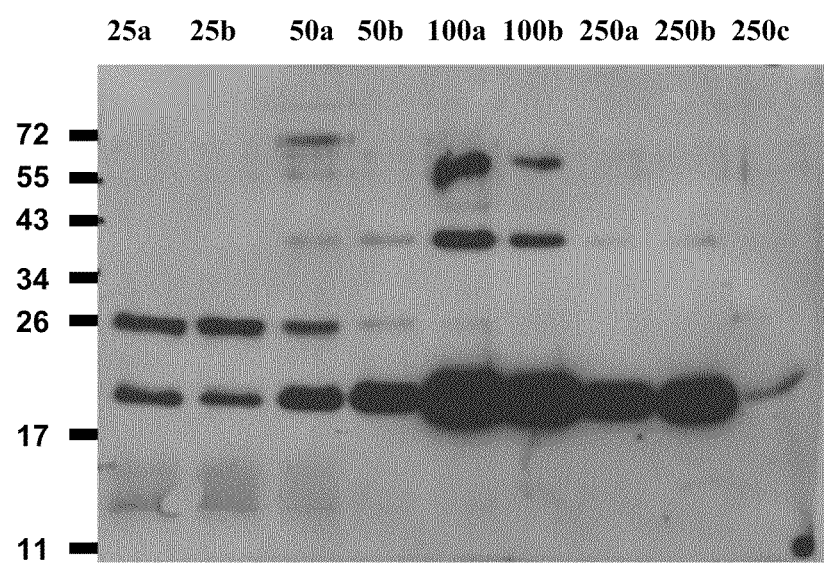
FIG. 4.

FIG. 4 shows detection by Western blotting of the presence of protein-6X-histidine in the various bacterial fractions obtained after purification.

40 μl of each fraction obtained after elution of the anti-6X-histidine tag column is deposited on a 16% polyacrylamide gel. Electrophoresis is carried out in migration buffer (192 mM glycine, 25 mM Tris-HCl pH 6.8 and 0.1% SDS) at 18 mA, in the presence of molecular weight markers (Amersham) using the Mini-Protean 3 migration system (Biorad). The proteins separated in the gel are transferred on a PVDF membrane (Biorad) for 60 min at 70 V. Non-specific binding is blocked by incubation of the membrane for 120 min at 37° C. and with stirring, in a saline solution of Tris+0.1% Tween-20 (TBS-T) containing 5% skimmed milk. The membrane is then incubated overnight at 4° C. with an anti-6X-histidine tag monoclonal antibody (Cell Signaling) diluted to 1/1000 in TBS-T. After 3 washings of 5 min in TBS-T, the membrane is incubated for 60 min at room temperature in an anti-mouse antibody coupled with peroxidase (Jackson Laboratories) diluted to 1/10,000. The membrane is again washed three times for 5 min in TBS. The result is visualised by the chemiluminescence technique using the ECL kit (Amersham).

The presence of protein is observed in the various fractions. The principal band obtained with a molecular weight of roughly 19 kDa corresponds to the monomeric form of the protein. Bands can also be observed in certain fractions corresponding to proteins with molecular weights of 26 kDa, 43 kDa and 60 kDa.

3. Demonstration of its Biological Activity: Platelet Aggregation

The platelet binding activity of the inventive protein is evaluated by aggregometry. Blood samples in citrate tubes, collected from healthy volunteer donors after signed consent, are centrifuged at 150 g for 15 minutes in order to obtain platelet-rich plasma (PRP). The concentration is adjusted to 300 giga/L. Aggregation tests are carried out using a Regulest® platelet aggregometer, with stirring (1000 rpm) at 37° C. This technique is based on photometric reading according to the Born method which consists in measuring the evolution of the light transmission through the PRP, which begins as a turbid medium, in response to a platelet activator. If platelet aggregates are formed, the medium clears up and an increase in light transmission is observed. A molecule is considered to have a pro-aggregating effect when an increase of more than 30% is observed in this transmission associated with a break in the slope corresponding to this clearing.

Figure 5:
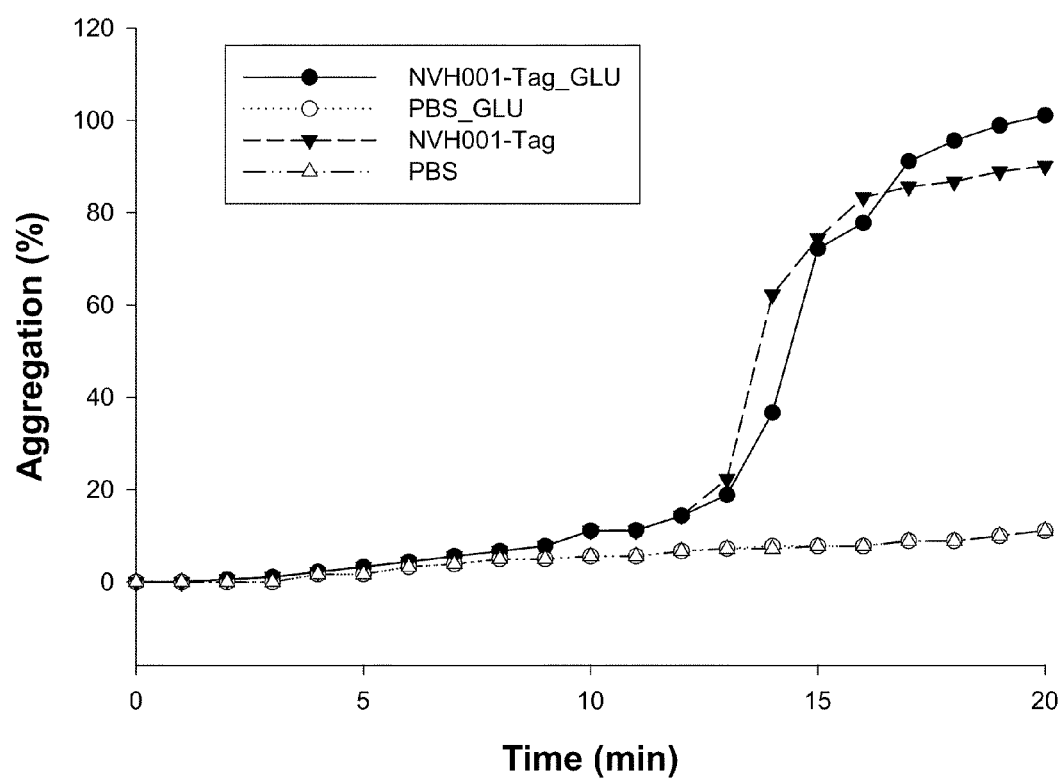
FIG. 5.

FIG. 5 shows platelet aggregation induced by the protein produced in bacteria.

The various fractions eluted from the anti-6X-histidine tag column containing the protein detected by Western blotting are collected and a lyophilisate is obtained by centrifugation. Part of this lyophilisate is incubated in the presence of 0.25% glutaraldehyde for 3 hours at 4° C. and then dialysed overnight against 1×PBS at 4° C. before its use in aggregometry.

The reaction mixture is composed of 290 μl PRP to which is added 30 μl PBS containing the protein. Platelet response is measured for 25 minutes. The lines marked -○- and -∇- show the response obtained after the adding of a solution of PBS and of dialysed PBS-glutaraldehyde, respectively: no aggregation is observed. The adding of PBS containing the protein not aggregated by glutaraldehyde (-▼-) or aggregated by glutaraldehyde and dialysed (-●-) shows significant aggregation 10 minutes after they were added. This aggregation reaches 90% (-▼-) and 100% (-●-), respectively, after 20 minutes.

D. Production of Anti-Protein of Interest Antibody in Rabbit

1. The protein is produced in large quantity in BL21 bacteria as previously described.

2. Two rabbits are immunised 4 times at 3-week intervals, that is to say at D0, D21, D42 and D63, with the purified protein supplemented (v/v) with Freund's adjuvant.

3. The rabbits are sacrificed at the end of the protocol at D89 and the sera are recovered by centrifugation after exsanguination of the animals.

4. The IgG are purified by affinity chromatography on a specific column in order to eliminate plasma proteins.

Figure 6:
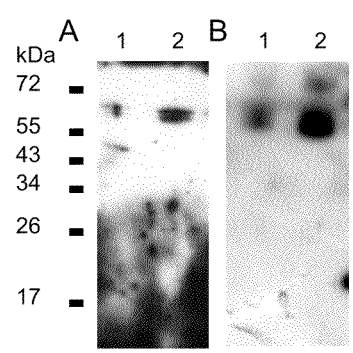
FIG. 6.

FIG. 6 shows the validation by Western blotting of the specificity of the rabbit serum obtained after 89 days of immunisation.

10 μl of two preparations of proteins produced in bacteria, whose aggregating activity was validated by aggregometry, is deposited on a 16% polyacrylamide gel. Electrophoresis is carried out in migration buffer (192 mM glycine, 25 mM Tris-HCl pH 6.8 and 0.1% SDS) at 18 mA, in the presence of molecular weight markers (Amersham) using the Mini-Protean 3 migration system (Biorad). The proteins separated in the gel are transferred on a PVDF membrane (Biorad) for 60 min at 70 V. Non-specific binding is blocked by incubation of the membrane for 120 min at 37° C. and with stirring, in a saline solution of Tris+0.1% Tween-20 (TBS-T) containing 5% skimmed milk. The membrane is then incubated overnight at 4° C. either with rabbit serum, withdrawn at D89 of the immunisation protocol and diluted to 1/100, or with an anti-6X-histidine tag monoclonal antibody (Cell Signaling) diluted to 1/1000 in TBS-T. After 3 washings of 5 min in TBS-T, the membrane is incubated for 60 min at room temperature in an anti-mouse or anti-rabbit antibody coupled with peroxidase (Jackson Laboratories) diluted to 1/10,000. The membrane is again washed three times for 5 min in TBS. The result is visualised by the chemiluminescence technique using the ECL kit (Amersham).

Visualisation shows the presence of a double band, present in the two protein preparations (A, wells 1 and 2), with a molecular weight of 60 kDa. This band is also detected by the anti-6X-histidine tag antibody, showing that it is indeed the inventive protein (B, wells 1 and 2). It should be noted that we no longer observe the other bands detected by the anti-6X-histidine tag antibody on the purified fractions of bacteria. This result suggests that immunisation was only effective for the multimeric form of the inventive protein or that the inventive protein assembles into a multimer once purified.

References

Asselin et al., Biochem J. 1999 Apr. 15; 339(Pt 2): 413-8
Born et al., Nature 1962 June, 194: 927-9
Boudko and Engel, J Mol Biol. 2004 Jan. 30; 335(5): 1289-97
Bulleid et al., EMBO J. 1997 Nov. 17; 16(22): 6694-701
Bulleid et al., Biochem J. 1996 Jul. 1; 317(Pt 1): 195-202
Farndale et al., Biochem Soc Trans. 2008 April; 36(Pt 2): 241-50
Hulmes D J, J Struct Biol. 2002 January-February; 137(1-2): 2-10
Jarvis et al., Blood. 2008 May 15; 111(10): 4986-96
Kim et al., J Biol Chem. 2005 Sep. 16; 280(37): 32512-20
Lisman T et al., Blood. 2006 Dec. 1; 108(12): 3753-6
McAlinden et al., J Biol Chem. 2003 Oct. 24; 278(43): 42200-7
Monnet E et al., J Biol Chem. 2000 Apr. 14; 275(15): 10912-7
Morton et al., Biochem J. 1995 Mar. 1; 306(Pt 2): 337-44
Olsen et al., Adv Drug Deliv Rev. 2003 Nov. 28; 55(12): 1547-67
Pires et al., Eur J Med Chem. 2007 May; 42(5): 694-701
Raynal et al., J Biol Chem. 2006 Feb. 17; 281(7): 3821-31
Ruggiero and Koch, Methods. 2008 May; 45(1): 75-85
Smethurst et al., J Biol Chem. 2007 Jan. 12; 282(2): 1296-304
Verkleij et al., Blood. 1998 May 15; 91(10): 3808-16

The invention claimed is:

1. An isolated polypeptide wherein said polypeptide has the sequence of the polypeptide of SEQ ID NO:1 or the polypeptide of position 25 to position 152 of SEQ ID NO:1.

2. A drug composition comprising a polypeptide according to claim 1.

3. The composition according to claim 2 for the treatment of thrombotic diseases.

4. The composition according to claim 2 for the treatment of disorders of haemostasis.

5. The composition according to claim 2 for use as a cicatrisation agent.

6. A cosmetic composition comprising the polypeptide according to claim 1.

* * * * *